(12) United States Patent
Wu et al.

(10) Patent No.: US 6,946,153 B2
(45) Date of Patent: Sep. 20, 2005

(54) **ANTI-FUNGAL PHARMACEUTICAL COMPOSITIONS COMPRISING AN ACTIVE INGREDIENT PREPARED FROM *ZINGIBER OFFICINALE***

(75) Inventors: Tian-Shung Wu, Tainan (TW); Sheng-Chu Kuo, Taichung (TW); Che-Ming Teng, Taipei (TW); Feng-Nien Ko, Taipei (TW)

(73) Assignee: Medical and Pharmaceutical Industry Technology and Development Center, Taipei (TW)

( * ) Notice: Subject to any disclaimer, the term of this patent is extended or adjusted under 35 U.S.C. 154(b) by 324 days.

(21) Appl. No.: 10/438,233

(22) Filed: May 14, 2003

(65) Prior Publication Data

US 2003/0203059 A1 Oct. 30, 2003

Related U.S. Application Data

(63) Continuation of application No. 09/887,488, filed on Jun. 22, 2001, now abandoned, which is a continuation-in-part of application No. 09/648,662, filed on Aug. 26, 2000, now Pat. No. 6,274,177.

(51) Int. Cl.$^7$ ............................................. A61K 35/78
(52) U.S. Cl. ........................ 424/756; 424/74; 424/773; 514/864
(58) Field of Search ................................. 424/756, 773, 424/74; 514/864

(56) References Cited

U.S. PATENT DOCUMENTS 6,274,177 B1 * 8/2001 Wu et al. .................... 424/756

* cited by examiner

Primary Examiner—Herbert J. Lilling
(74) Attorney, Agent, or Firm—Jackson Walker L.L.P.

(57) ABSTRACT

A method of treating a patient suffering a disease associated with *Trichophyton mentagrophytes* or *Pityrosporum ovale* by applying topically an anti-fungal pharmaceutical composition which is prepared from *Zingiber officinale*, includes the following steps: preparing a crude liquid from rhizomes of ginger by extraction with an organic solvent or supercritical $CO_2$, or by distillation with steam; introducing the crude liquid to a reverse phase chromatography column, and eluting the column with water, a first eluent and a second eluent having a polarity weaker than that of the first eluent but stronger than that of chloroform, so that a first eluate resulting from elution of the first eluent and a second eluate resulting from elution of the second eluent are obtained; removing the first eluent and the second eluent from the first eluate and the second eluate by evaporation, respectively, so that a first concentrated eluate and a second concentrated eluate are obtained as the potent extract.

29 Claims, No Drawings

ANTI-FUNGAL PHARMACEUTICAL COMPOSITIONS COMPRISING AN ACTIVE INGREDIENT PREPARED FROM ZINGIBER OFFICINALE

CROSS-REFERENCE TO RELATED APPLICATION

The present application is a continuation application of U.S. patent application Ser. No. 09/887,488, filed Jun. 22, 2001, abandoned which is a continuation-in-part application of U.S. patent application Ser. No. 09/648,662, filed Aug. 26, 2000 now U.S. Pat No. 6,274,177. The above-listed applications of Ser. Nos. 09/648,662 and 09/887,488 are commonly assigned with the present invention and the entire content of these applications is incorporated herein by reference.

FIELD OF THE INVENTION

The present invention is related to a method of treating a patient suffering a disease associated with *Trichophyton mentagrophytes* or *Pityrosporum ovale* by applying topically an anti-fungal pharmaceutical composition prepared from *Zingiber officinale*.

BACKGROUND OF THE INVENTION

Chinese crude drugs or spices eg. *Zingiber officinale, Eugenia caryophyllata, Allium sativum*, have been used in medicine and in flavoring foods. Crude ginger is used as an anti-emetic and expectorant, an anti-tussive and accelerator of the digestive organs. Semi-dried old crude ginger is also used for stomachache, chest pain, low back pain, cough, common cold and as a cure for a form of edema being called "stagnate of water". Zingerone is the major component which accounts for the spicy character of ginger; gingerol and shogaol are other pungent components in ginger. Gingerol has cardio-tonic action, suppresses the contraction of isolated portal veins in mice, and modulates the eicosanoid-induced contraction of mouse and rat blood vessels. Shogaol exhibits pressor response. Both gingerol and shogaol are mutagenic, whereas zinger and zingerone have been found to exhibit anti-mutagenic activity. Shogaol has inhibitory activity on the carrageenin-induced paw edema and platelet aggregation [U.S. Pat. No. 5,804,603, Background of the Invention].

Heretofore, many reports have shown that *Zingiber officinale* exhibits various physiological activities. Typical examples include a cancer metastasis suppressing agent disclosed in Japan patent publication No. 7-258104; a synthesis promoter for neurotropic factor, which is effective for nerve deteriorative diseases such as Alzheimer's dementia or Parkinson's disease, disclosed in Japan patent publication No. 7-25777; an anti-rheumatic agent disclosed in Japan patent publication No. 6-293653, U.S. Pat. Nos. 5,494,668 and 5,683,698; an anti-microbial composition disclosed in Japan patent publication No. 6-227931; and an analgesic composition disclosed in Japan patent publication No. 6-107556. Ginger contains 1–4% essential oil (oleoresin). During the last 45 years many chemical investigations have been carried out on the constituents of the essential oil. Altogether more than 200 different volatiles have been identified in essential oil wherein the pharmacological activity is confined. The essential oil contains a mixture of various terpenes as well as some other non-terpenoid compounds. Although this is mostly speculative, the experimental data and observations suggest that ginger inhibits both the cyclooxygenase and lypoxygenase products, i.e. it can be a dual inhibitor of eicosanoid synthesis. In all 56 patients (28 with rheumatoid arthritis, 18 with osteoarthritis and 10 with muscular discomfort) used powdered ginger against their afflictions. Amongst the arthritis patients more than three-quarters experienced, to varying degrees, relief in pain and swelling. All the patients with muscular discomfort experienced relief in pain. None of the patients reported adverse effects during the period of ginger consumption which ranged from 3 months to 2.5 years. (Srivastava and Mustafa; Medical Hypotheses; 1992; 39 342–348)

Non-steroidal anti-inflammatory drugs have three major actions, all of which are related to inhibition of cyclo-oxygenase resulting in decreased formation of prostanoids. Firstly, an anti-inflammatory action achieved by reduced production of vasodilator prostaglandins ($PGE_2$, $PGI_2$) which means less vasodilation and, indirectly less edema. Secondly, an analgesic effect achieved by reduced prostaglandin production (less sensitization of nociceptic nerve endings to the inflammatory mediators bradykinin and 5-hydroxytryptamine). Thirdly, an antipyretic effect which is probably due to a decrease in the mediator $PGE_2$ generated in response to inflammatory pyrogens, much as interleukin-1. Since ginger inhibits prostanoid synthesis and also products of 5-lipoxygenase, its ameliorative effects in arthritis and muscular discomforts could be related to reduced formation of prostanoids and leukotrienes. Because of such a possibility a decrease in the carageenan-induced edema formation in the rat's paw after 3 g of ginger extract administration has been demonstrated and the potency of the extract in the acute inflammation test appears to be comparable to that exhibited by acetyl salicylic acid reported in the same study (Mascolo N. et al., Journal of Ethnopharmocology 1989, 27, 129–140).

Dermatophytes, especially *Trichophyton rubrum* and *Trichophyton mentagrophytes*, are the usual pathogens of onychomycosis and tinea pedis [Roberts D T., British Journal of Dermatology. 141 Supple 56:1–4, 1999 November; Roldan Y B. et al., Mycoses, 43(5):181-3, 2000]. *Pityrosporum ovale* (*Malassezia furfur*) is the etiological agent of pityriasis vesicolor, *Pityrosporum folliculitis* and *Malassezia intertrigo*. Several studies indicate a strong association of *Pityrosporum ovale* with seborrheic dermatitis and dandruff, a milder form of seborrheic dermatitis [Nenoff P. et al., Dermatology. 191(4):311–4, 1995; Bulmer A C. et al., Mycopathologia, 147(2)63–5, 1999].

SUMMARY OF THE INVENTION

The present invention provides a method of treating a patient suffering a disease associated with *Trichophyton mentagrophytes* or *Pityrosporum ovale* by applying topically an anti-fungal pharmaceutical composition prepared from extracts from rhizomes of ginger. The extracts are prepared by extracting rhizomes of ginger with an organic solvent (such as ethyl ether, acetone, methanol and ethanol) or supercritical $CO_2$, or by steam distilling rhizomes of ginger to obtain a crude liquid, and subjecting said crude liquid to a reverse phase chromatography to obtain the extracts containing shogaols, gingerols and/or dehydrogingerdione.

DETAILED DESCRIPTION OF THE INVENTION

As introduced in the Background of the Invention, ginger has been used for anti-inflammation and pain relief.

The present invention provides an effective method of treating a patient suffering a disease associated with *Tricho-*

*phyton mentagrophytes* or *Pityrosporum ovale* by applying topically an anti-fungal pharmaceutical composition comprising a therapeutically effective amount of a product prepared from rhizomes of *Zingiber officinale*, as an active ingredient, mixed with a pharmaceutically acceptable carrier or diluent. The anti-fungal pharmaceutical composition is a product potent in antifungal activity prepared from rhizomes of ginger. The potent product prepared in accordance with the method of the present invention has a substantially constant composition, so that the pharmacological effects thereof are definite.

The effective method of preparing product potent in antifungal activity from rhizomes of ginger according to the present invention comprises the following steps:

a) preparing a crude liquid from rhizomes of ginger;

b) introducing the crude liquid to a reverse phase chromatography column, and eluting the column with water, a first eluent and a second eluent in sequence, said second eluent having a polarity weaker than that of the first eluent but stronger than that of chloroform, so that a first eluate resulting from elution of the first eluent and a second eluate resulting from elution of the second eluent are obtained;

c) removing the first eluent from the first eluate by evaporation, so that a first concentrated eluate is obtained and is able to be used as the potent product; and d) removing the second eluent from the second eluate by evaporation, so that a second concentrated eluate is obtained and is able to be used as the potent product;

wherein step a) comprises steps i) to iv), or comprises step I), step I'), or step I"), wherein said steps i) to iv) are:

i) shedding fresh rhizomes of ginger and filtering the resulting mixture to obtain a filtrate and a residue;

ii) extracting the filtrate with a first organic solvent, recovering the resulting extraction solution of the first organic solvent, and evaporating the first organic solvent from the extraction solution to obtain a first concentrated extraction solution;

iii) extracting the residue with a second organic solvent, recovering the resulting extraction solution of the second organic solvent, and evaporating the second organic solvent from the extraction solution to obtain a second concentrated extraction solution; and iv) combining the first concentrated extraction solution and the second concentrated extraction solution to obtain the crude liquid;

said step I) is:

I) extracting powder of dried rhizomes of ginger with the second organic solvent, recovering the resulting extraction solution of the second organic solvent, and evaporating the second organic solvent from the extraction solution to obtain the crude liquid;

said step I') is:

I') steam distilling powder of dried rhizomes of ginger, and concentrating the resulting distillate by evaporation to obtain the crude liquid; and said step I") is:

I") extracting powder of dried rhizomes of ginger with supercritical $CO_2$, recovering the resulting extraction solution of the supercritical $CO_2$, and evaporating $CO_2$ from the extraction solution to obtain the crude liquid.

The product potent in antifungal activity prepared according to the method of the present invention preferably comprises 0–10 mg 6-shogaol per gram of the product, 1–150 mg 6-gingerol per gram of the product, and 0–40 mg 6-dehydrogingerdione per gram of the product.

The present invention also provides a pharmaceutical composition potent in antifungal activity comprising a therapeutically effective amount of said crude liquid prepared in step a) of the method of the present invention, as an active ingredient, in admixture with a pharmaceutically acceptable carrier or diluent for the active ingredient.

The present invention also provides a pharmaceutical composition potent in antifungal activity comprising a therapeutically effective amount of said product prepared according to the method of the present invention, as an active ingredient, in admixture with a pharmaceutically acceptable carrier or diluent for the active ingredient. Preferably, said product prepared according to the method of the present invention is the first concentrated eluate prepared in step c). Alternatively, said product prepared according to the method of the present invention is the second concentrated eluate prepared in step d).

Preferably, said first eluent is methanol, and said second eluent is acetone.

Preferably, step a) of the method of the present invention comprises steps i) to iv).

Preferably, said first organic solvent is ethyl ether.

Preferably, said second organic solvent is acetone, methanol, ethanol or a combination thereof. More preferably, said second organic solvent is acetone.

Preferably, step a) of the method of the present invention comprises step I).

Preferably, step a) of the method of the present invention comprises step I').

Preferably, step a) of the method of the present invention comprises step I").

A suitable reverse phase chromatography column for use in the method of the present invention includes (but not limited thereto) a reverse phase chromatography column packed with a porous resin, for examples Diaion HP-20 (Mitsubishi Co.), Sephadex LH-20 (Pharmicia Co.) and RP-18 (Nacalai tesque Co.).

The pharmaceutical composition potent in antifungal activity of the present invention is preferably applied topically, for examples as a shampoo, a bath gel, soap, a body lotion, a body cream and a detergent. Preferably, the pharmaceutical composition potent in antifungal activity of the present invention is used in the treatment of diseases associated with *Trichophyton mentagrophytes* or *Pityrosporum ovale*, including but are not limited to tinea pedis, tinea capitis, tinea cruris, tinea glabrosa, onychomycosis, pityriasis capitis, pityriasis vesicolor, pityrosporum folliculitis, seborrheic dermatitis and dandruff. In particular, the antifungal pharmaceutical composition of the present invention is in the form of a shampoo for use in the treatment of dandruff.

Without further elaboration, it is believed that the above description has adequately enabled the present invention. The following specific examples are, therefore, to be construed as merely illustrative, and not limitations on the remainder of the disclosure in any way whatsoever.

Determination of Active Ingredients

In the following examples, high performance liquid chromatography (abbreviated as HPLC) was used to determine the active ingredients of the products prepared therein. HPLC spectra were recorded on a HPLC instrument (HPLC Shimadzu LC-10AT, Japan) using a Cosmosil 5C-18 column (250 mm×4.6 mm, packed with particles having 5 $\mu$m diameter) by an elution method. An HPLC sample was prepared by diluting an appropriate amount of a product with a mobile phase solution (hydrogen cyanide:water= 65:35, V/V) to 25 ml, and filtered with a 0.25 μm membrane. The filtrate was introduced into the HPLC column, and eluted with the mobile phase solution. An UV detector (Shimadzu SPD-6AV, Japan) was used to detect the absorption of the eluate at 230 nm.

EXAMPLE 1

2100 g of fresh rhizomes of ginger were shredded and filtered to obtain a filtrate and a residue. 500 ml of the filtrate was extracted with 500 ml ethyl ether three times, the organic phase layers were separated from the aqueous phase layers, and combined. Ethyl ether was evaporated from the combined extraction solution in vacuo to obtain a concentrated ethyl ether extraction product (I-OE). The ginger residue was extract with 3000 ml acetone three times, the extraction solutions were recovered by filtration, and combined. Acetone was evaporated from the combined extraction solution in vacuo to obtain a concentrated acetone extraction product (I-O) (14.5 g). To a reverse phase chromatography column 300 mm×30 mm packed with 180 g Diaion HP-20 resin having a diameter of 500 μm–800 μm, 7 g of a mixture of the concentrate ethyl ether extraction product (I-OE) and the concentrated acetone extraction product (I-O) was injected. 1500 ml water, 2500 ml methanol, 2000 ml acetone and 2000 ml chloroform were used to carry out elution. The water eluate, methanol eluate, acetone eluate and chloroform eluate were collected separately, and concentrated in vacuo to obtain 0.27 g concentrated water eluate (I-OW), 1.45 g concentrated methanol eluate (I-OM), 2.68 g concentrated acetone eluate (I-OA), and 0.83 g concentrated chloroform eluate (I-OC). The amounts (mg) of 6-shogaol, 6-gingerol and 6-dehydrogingerdione per gram of the I-O, I-OM and I-OA determined by HPLC are listed in Table 1.

TABLE 1

| Content (mg/g) | I-O | I-OM | I-OA |
| --- | --- | --- | --- |
| 6-shogaol | 1.10 ± 0.14 | 1.15 ± 0.0 | — |
| 6-gingerol | 59.98 ± 0.99 | 103.37 ± 8.57 | 2.51 ± 0.89 |
| 6-dehydrogingerdione | 7.68 ± 0.42 | 8.94 ± 0.41 | — |

EXAMPLE 2

500 g of shade dried rhizomes of ginger were pulverized and the resulting powder was extracted with 30 L acetone trice (each time with 10 L). The three extraction solutions were combined together after filtration, and then concentrated in vacuo to obtain 24 g of concentrated acetone extraction product (II-O). To a reverse phase chromatography column packed with 600 g Diaion HP-20 resin 20 g of the concentrated acetone extraction product (II-O) was injected, which was then eluted with 4 L water, 6.5 L methanol, 15 L acetone and 5 L chloroform in sequence. The water eluate, methanol eluate, acetone eluate and chloroform eluate were collected separately, and concentrated in vacuo to obtain 2.5 g concentrated water eluate (II-OW), 7.1 g concentrated methanol eluate (II-OM), 6.9 g concentrated acetone eluate (II-OA), and 3.5 g concentrated chloroform eluate (II-OC). The amounts (mg) of 6-shogaol, 6-gingerol and 6-dehydrogingerdione per gram of the II-O, II-OM and II-OA determined by HPLC are listed in Table 2.

TABLE 2

| Content (mg/g) | II-O | II-OM | II-OA |
| --- | --- | --- | --- |
| 6-shogaol | 1.98 ± 0.00 | 4.96 ± 0.00 | — |
| 6-gingerol | 43.06 ± 0.84 | 70.87 ± 1.85 | 2.54 ± 0.00 |
| 6-dehydrogingerdione | 9.33 ± 0.85 | 19.15 ± 4.57 | 2.35 ± 0.28 |

EXAMPLE 3

10 Kg of shade dried rhizomes of ginger were pulverized and the resulting powder was steam distilled for five hours. The distillate was concentrated in vacuo to obtain 410 g of concentrated distillate (III-O). To a reverse phase chromatography column packed with 600 g Diaion HP-20 resin 20 g of the concentrated distillate (III-O) was injected, which was then eluted with 4.5 L water, 4.5 L methanol, 3 L acetone and 5 L chloroform in sequence. The water eluate, methanol eluate, acetone eluate and chloroform eluate were collected separately, and concentrated in vacuo to obtain 0.03 g concentrated water eluate (III-OW), 14.5 g concentrated methanol eluate (III-OM), 0.85 g concentrated acetone eluate (III-OA), and 0.2 g concentrated chloroform eluate (III-OC). The concentrated distillate (III-O) contains no 6-shogaol, 6-gingerol and 6-dehydrogingerdione determined by HPLC.

EXAMPLE 4

10 g of powder of shade dried rhizomes of ginger was extracted with 1000 ml acetone at 50° C. for two hours. The extraction solution was separated and concentrated in vacuo (40° C., 75 mmHg) to obtain a concentrated acetone extraction product (IV-b). The color and viscosity of the product (IV-O) together with its yield are listed in Table 3.

EXAMPLE 5

10 g of powder of shade dried rhizomes of ginger was steam distilled, and the oily distillate after being separated from the aqueous distillate was freeze dried to obtain an oily extract (V-O). The color and viscosity of the oily extract (V-O) together with its yield are listed in Table 3

EXAMPLE 6

To 10 g of powder of shade dried rhizomes of ginger in a 250 ml extraction chamber $CO_2$ was introduced at a flow rate of 45 L/min, wherein the chamber pressure was controlled at 2500 to 4000 psia with a high pressure pump (Model No. EK-1, LEWA Co., US) and the chamber temperature was maintained at 35–60° C. with a heat exchanger (Model No. H-2410, HOTEC Co., US) and an exterior circulation system. The extraction was stopped when the volume of $CO_2$ introduced reached 300 L, and a supercritical $CO_2$ extraction product (VI-O) was obtained after evaporation of $CO_2$. The color and viscosity of the product (VI-O) together with its yield are listed in Table 3. The contents of pungent components determined by HPLC are listed in Table 4.

TABLE 3

|  | IV-O | V-O | VI-O |
| --- | --- | --- | --- |
| L* | 87.6 | 80.4 | 96.3 |
| A* | −9.1 | −0.1 | −9.6 |

TABLE 3-continued

|  | IV-O | V-O | VI-O |
|---|---|---|---|
| B* | 31.1 | 9.6 | 22.0 |
| Viscosity (cPs) | 15.6 | 11.8 | 12.1 |
| Yield (%) | 3.8 | 2.2 | 3.9 |

*the values of L, A, and B were determined by using a Σ90 color measuring system, (Nippon Denshoku Inc, Co., Ltd., Japan), wherein L represents lightness, A is the red/green difference and B is the yellow/blue difference.

TABLE 4

| Content (mg/g) | VI-O |
|---|---|
| 6-shogaol | 17.30 ± 0.00 |
| 6-gingerol | 26.29 ± 0.00 |
| 6-dehydrogingerdione | 19.20 ± 1.19 |

EXAMPLE 7

Evaluation of Inhibitory Activity on *Trichophyton mentagrophytes* or *Pityrosporum ovale*

Anti-*Trichophyton mentagrophytes* Assay

Minimum inhibitory concentration (MIC) of ginger extract was determined and conducted according to the method previously described by Edwards, J. R. et al. (Edwards, J. R. et al., Antimicrobial Agents Chemotherapy 33: 215–222, 1989). The test substance was dissolved and serially diluted in solvent (100% DMSO) to desired stock concentrations. For each concentration tested, a 0.01 ml aliquot was added to a 48-well plate containing 0.99 ml of Potato Dextrose Broth (DIFCO, U.S.A.) with $10^3$–$10^4$ CFU/ml of *Trichophyton mentagrophytes* (ATCC 9533). The plates were incubated at 28° C. for 72 hours and then visually examined and scored. Vehicle-control was used as blank control. Each concentration was evaluated in duplicate. The results are shown in Table 5.

Anti-*Pityrosporum ovale* Assay

Minimum inhibitory concentration (MIC) of ginger extract was determined and conducted by the method as mentioned above (Edwards, J. R. et al., Antimicrobial Agents Chemotherapy 33: 215–222, 1989). The test substance was dissolved and serially diluted in solvent (100% DMSO) to desired stock concentrations. For each concentration tested, a 0.01 ml aliquot was added to a 48-well plate containing 0.99 ml of Fluid Sabouraud Medium (DIFCO, U. S. A.) with $10^3$–$10^4$ CFU/ml of *Pityrosporum ovale* (ATCC 38593). The plates were incubated at 37° C. for 48 hours and then visually examined and scored. Vehicle-control was used as blank control. Each concentration was evaluated in duplicate. The results are shown in Table 5.

TABLE 5

The inhibitory effects of ginger extracts on *Pityrosporum ovale* (Po) and *Trichophyton mentagrophytes* (Tm)

| Ginger extract[a] | MIC (μg/ml) | |
|---|---|---|
|  | Po | Tm |
| I-O | 100 | 30 |
| I-OM | 100 | 30 |
| II-O | 500 | 30 |
| II-OC | 100 | 30 |
| II-OM | 100 | 30 |
| III-O | 500 | 100 |
| Blank control | —[b] | —[b] |

[a] Prepared in Examples 1, 2 and 3
[b] no inhibitory effect upon growth

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A method of treating a patient suffering a disease associated with Trichophyton mentagrophytesor *Pityrosporum ovale* by applying topically an anti-fungal pharmaceutical composition comprising a therapeutically effective amount of a product prepared from rhizomes of *Zingiber officinale*, as an active ingredient, in admixture with a pharmaceutically acceptable carrier or diluent for the active ingredient, wherein said product is prepared by the following steps:

a) preparing a crude liquid from rhizomes of *Zingiber officinale*;

b) introducing the crude liquid to a reverse phase chromatography column, and eluting the column with water, a first eluent and a second eluent in sequence, said second eluent having a polarity weaker than that of the first eluent but stronger than that of chloroform, so that a first eluent resulting from elution of the first eluent and a second eluate resulting from elution of the second eluent are obtained;

c) removing the first eluent from the first eluate by evaporation, so that a first concentrated eluate is obtained and is able to be used as the product; and d) removing the second eluent from the second eluate by evaporation, so that a second concentrated eluate is obtained and is able to used as the product;

wherein step a) comprises steps i) to iv), or comprises step I), step I'), or step I"), wherein said steps i) to iv) are:

i) shedding fresh rhizomes of *Zingiber officinale* and filtering the resulting mixture to obtain a filtrate and a residue;

ii) extracting the filtrate with a first organic solvent, recovering the resulting extraction solution of the first organic solvent, and evaporating the first organic solvent from the extraction solution to obtain a first concentrated extraction solution;

iii) extracting the residue with a second organic solvent, recovering the resulting extraction solution of the second organic solvent, and evaporating the second organic solvent from the extraction solution to obtain a second concentrated extraction solution; and iv) combining the first concentrated extraction solution and the second concentrated extraction solution to obtain the crude liquid;

said step I) is:

I) extracting powder of dried rhizomes of *Zingiber officinale* with the second organic solvent, recovering the resulting extraction solution of the second organic solvent, and evaporating the second organic solvent from the extraction solution to obtain the crude liquid;

said step I') is:

I') steam distilling powder of dried rhizomes of *Zingiber officinale*, and concentrating the resulting distillate by evaporation to obtain the crude liquid; and said step I") is:

I") extracting powder of dried rhizomes of *Zingiber officinale* with supercritical $CO_2$, recovering the resulting extraction solution of the supercritical $CO_2$, and evaporating $CO_2$ from the extraction solution to obtain the crude liquid.

2. The method according to claim 1, wherein the product as the active ingredient comprises 0–10 mg6-shogaol per gram of the product, 1–150mg6-gingerol per gram of the product, and 0–40 mg 6-dehydrogingerdione per gram of the product.

3. The method according to claim 1, wherein said first eluent is methanol, and said second eluent is acetone.

4. The method according to claim 3, wherein step a) comprises steps i) to iv).

5. The method according to claim 4, wherein said first organic solvent is ethyl ether.

6. The method according to claim 4, wherein said second organic solvent is acetone, methanol, ethanol or a combination of them.

7. The method according to claim 6, wherein said second organic solvent is acetone.

8. The method according to claim 3, wherein step a) comprises step I).

9. The method according to claim 8, wherein said second organic solvent is acetone, methanol, ethanol or a combination of them.

10. The method according to claim 9, wherein said second organic solvent is acetone.

11. The method according to claim 3, wherein step a) comprises step I').

12. The method according to claim 3, wherein step a) comprises step I").

13. The method according to claim 1, wherein said reverse phase chromatography column is packed with a porous resin.

14. A method of treating a patient suffering a disease associated with *Trichophyton mentagrophytes* or *Pityrosporum ovale* by applying topically an anti-fungal pharmaceutical composition comprising a therapeutically effective amount of a crude liquid prepared from rhizomes of *Zingiber officinale*, as an active ingredient, in admixture with a pharmaceutically acceptable carrier or diluent for the active ingredient, wherein said crude liquid is prepared by a process comprising steps i) to iv), or comprising step I), step I') or step I"), wherein said steps i) to iv) are:

i) shedding fresh rhizomes of *Zingiber officinale* and filtering the resulting mixture to obtain a filtrate and a residue;

ii) extracting the filtrate with a first organic solvent, recovering the resulting extraction solution of the first organic solvent, and evaporating the first organic solvent from the extraction solution to obtain a first concentrated extraction solution;

iii) extracting the residue with a second organic solvent, recovering the resulting extraction solution of the second organic solvent and evaporating the second organic solvent from the extraction solution to obtain a second concentrated extraction solution; and iv) combining the first concentrated extraction solution and the second concentrated extraction solution to obtain the crude liquid;

said step I) is:

I) extracting powder of dried rhizomes of *Zingiber officinale* with the second organic solvent, recovering the resulting extraction solution of the second organic solvent, and evaporating the second organic solvent front the extraction solution to obtain the crude liquid;

said step I') is:

I') steam distilling powder of dried rhizomes of *Zingiber officinale*, and concentrating the resulting distillate by evaporation to obtain the crude liquid; and said step I") is:

I") extracting powder of dried rhizomes of *Zingiber officinale* with supercritical $CO_2$, recovering the resulting extraction solution of the supercritical $CO_2$, and evaporating $CO_2$ from the extraction solution to obtain the crude liquid.

15. The method according to claim 14, wherein said process comprises steps i) to iv).

16. The method according to claim 15, wherein said first organic solvent is ethyl ether.

17. The method according to claim 16, wherein said second organic solvent is acetone, methanol, ethanol or a combination of them.

18. The method according to claim 17, wherein said second organic solvent is acetone.

19. The method according to claim 14, wherein said process comprises step I).

20. The method according to claim 19, wherein said second organic solvent is acetone, methanol, ethanol or a combination of them.

21. The method according to claim 20, wherein said second organic solvent is acetone.

22. The method according to claim 14, wherein said process comprises step I').

23. The method according to claim 14, wherein said process comprises step I").

24. The method according to claim 1, in which said disease is selected from the group consisting of tinea pedis, tinea capitis, tinea cruris, tinea glabrosa, onychomycosis, pityriasis capitis pityriasis vesicolor, pityrosporum folliculitis, seborrheic dermatitis and dandruff.

25. The method according to claim 1, which is in the form of a shampoo, a bath gel, soap, a body lotion, a body cream or a detergent.

26. The method according to claim 25, which is in the form of a shampoo for use in the treatment of dandruff.

27. The method according to claim 14, in which said disease is selected from the group consisting of tinea pedis, tinea capitis, tinea cruris, tinea glabrosa, onychomycosis, pityriasis capitis, pityriasis vesicolor, pityrosporum folliculitis, seborrheic dermatitis and dandruff.

28. The method according to claim 14, which is in the form of a shampoo, a bath gel, soap, a body lotion, a body cream or a detergent.

29. The method according to claim 28, which is in the form of a shampoo for use in the treatment of dandruff.

* * * * *